United States Patent [19]

Doerper et al.

[11] Patent Number: 5,180,811
[45] Date of Patent: Jan. 19, 1993

[54] PROTEINS HAVING A TNF ACTION COMPRISING TNF-FIBROMECTIN FUSION PROTEIN

[75] Inventors: Thomas Doerper, Bissersheim; Achim Moeller, Limburgerhof; Heinz Hillen, Ludwigshafen; Gerhard Keilhauer, Dannstadt-Schauernheim; Franz Emling, Ludwigshafen; Lothar Daum, Otterstadt, all of Fed. Rep. of Germany

[73] Assignee: BASF Aktiengesellschaft, Ludwigshafen, Fed. Rep. of Germany

[21] Appl. No.: 193,661

[22] Filed: May 13, 1988

[30] Foreign Application Priority Data

May 16, 1987 [DE] Fed. Rep. of Germany ....... 3716513

[51] Int. Cl.$^5$ ............................................. C07K 13/00
[52] U.S. Cl. .................................... 530/351; 530/395; 435/69.52; 435/69.7; 424/85.1; 930/144
[58] Field of Search ............................... 530/351, 395; 435/69.52, 69.7; 424/85.1; 930/144

[56] References Cited

U.S. PATENT DOCUMENTS 4,879,226 11/1989 Wallace et al. .................. 530/351
4,990,455 2/1991 Yamagashi et al. ............. 530/351

FOREIGN PATENT DOCUMENTS 0155549 9/1985 European Pat. Off. .
0207751 1/1987 European Pat. Off. .

OTHER PUBLICATIONS

Vogel et al., CA vol. 114, 1991, #137413d.
Proc. Nat. Acad. Science, vol. 72, No. 9, pp. 3666–3670, Sep. 1975, "An endotoxin–induced serum factor that . . .".
Lymphokines Reports, vol. 2, pp. 235–275, 1981, "A Forum for Immunoregulatory Cell Products".
The Journal of Biological Chemistry, vol. 260, pp. 2345–2354 (1985), "Human Tumor Necrosis Factor".
Nucleic Acids Research, vol. 13, No. 17, pp. 6359–6373, (1985).
The Journal of Cell Biology, vol. 94, pp. 369–377, (1982), "Fibronectins: Multifunctional Modular Glycoproteins".
The Journal of Biological Chemistry, vol. 257, No. 15, pp. 8557–8560, Aug. 10, 1982.
The Journal of Biological Chemistry, vol. 256, No. 18, pp. 9477–9482, Sep. 25, 1981.
Proc. National Academy Science, U.S.A. Oct. 1984 pp. 5985–5988 "Variants of the Cell Recognition site of Fibronectin that retain attachment–promoting activity".
Biochemistry, (1988) pp. 277–279 L. Stryer "Connective–tissue proteins".
Olsnes et al., Pharmac. Ther. vol. 15, 1982, pp. 355–381.
Tarernier et al., J. Mol. Biol., 211(2) 1990, pp. 493–502.
Sherblom et al., J. Biol. Chem. 263(11) 1988, pp. 5418–5424.

Primary Examiner—Garnette D. Draper
Attorney, Agent, or Firm—Oblon, Spivak, McClelland, Maier & Neustadt

[57] ABSTRACT

Derivatives of a tumor necrosis factor (TNF), which originate from a modification at the amino terminus of the TNF molecule are suitable for controlling diseases.

2 Claims, 2 Drawing Sheets

PROTEINS HAVING A TNF ACTION COMPRISING TNF-FIBROMECTIN FUSION PROTEIN

BACKGROUND OF THE INVENTION

1. Field of the Invention

The present invention relates to novel proteins having a TNF action, to the preparation thereof, and to the use thereof in therapy.

2. Discussion of the Background

Carswell et al. [Proc. Natl. Acad. Sci. USA 72,3666-3670, 1975] have reported that serum from endotoxin-treated animals which had previously been infected with the Calmette-Guerin (BCG) microbacteria strain brought about hemorrhagic necrosis in various mouse tumors. This activity was attributed to a tumor necrosis factor (TNF). TNF also has a cytostatic or cytotoxic action against a plurality of transformed cell lines in vitro, whereas normal human and animal cell lines are unaffected by this [Ruff and Gifford, Lymphokine Reports Vol. 2, pp 235-275, Academic Press, New York, 1981]. The biochemical characterization and the gene for human TNF have recently been described [Aggarwal et al., J. Biol. Chem. 260 (1985), 2345-2354; Nedwin et al., Nucl. Acids Res. 13 (1985), 6361-6373]. These data allow the following protein structure for mature human TNF to be deduced:

ValArgSerSerSerArgThrProSerAspLysProValAlaHisValValAlaAsnPro
GlnAlaGluGlyGlnLeuGlnTrpLeuAsnArgArgAlaAsnAlaLeuLeuAlaAsnGly
ValGluLeuArgAspAsnGlnLeuValValProSerGluGlyLeuTyrLeuIleTyrSer
GlnValLeuPheLysGlyGlnGlyCysProSerThrHisValLeuLeuThrHisThrIle
SerArgIleAlaValSerTyrGlnThrLysValAsnLeuLeuSerAlaIleLysSerPro
CysGlnArgGluThrProGluGlyAlaGluAlaLysProTrpTyrGluProIleTyrLeu
GlyGlyValPheGlnLeuGluLysGlyAspArgLeuSerAlaGluIleAsnArgProAsp
TyrLeuAspPheAlaGluSerGlyGlnValTyrPheGlyIleIleAlaLeu

Fibronectin is a glycoprotein which occurs in human plasma and has a molecular weight of about 450,000. It consists of two disulfide-linked polypeptide chains which contain a cell-binding domain [Hynes et al., J. Cell Biol. 95 (1982), 369-377]. The primary structure of this cell-binding domain was established by Pierschbacher et al., J. Biol. Chem. 257 (1982), 9593-9597. The fibronectin molecule is able using this domain to bind to a receptor on the surface of cells such as blood platelets of fibroblasts [Plow and Ginsberg, J. Biol. Chem. 256 (1981) 9477-9482].

Attachment of partial sequences from the cell-binding domain of human fibronectin to the amino terminus of mature human TNF results in hybrid proteins which have more advantageous properties than human TNF itself.

SUMMARY OF THE INVENTION

The invention relates to proteins having the following amino acid sequence:

Y—Val—X—(Ser)$_n$—ArgThrProSerAspLys

ProValAlaHisValValAlaAsnPro

GlnAlaGluGlyGlnLeuGlnTrpLeuAsnArg

ArgAlaAsnAlaLeuLeuAlaAsnGly

ValGluLeuArgAspAsnGlnLeuValValPro

SerGluGlyLeuTyrLeuIleTyrSer

GlnValLeuPheLysGlyGlnGlyCysProSer

ThrHisValLeuLeuThrHisThrIle

SerArgIleAlaValSerTyrGlnThrLysVal

AsnLeuLeuSerAlaIleLysSerPro

CysGlnArgGluThrProGluGlyAla

GluAlaLysProTrpTyrGluProIleTyrLeu

GlyGlyValPheGlnLeuGluLysGlyAspArg

LeuSerAlaGLuIleAsnArgProAsp

TyrLeuAspPheAlaGluSerGlyGlnValTyr

PheGlyIleIleAlaLeu.

in which n is 0, 1, 2, 3 or 4, X is the sequence or part thereof from the cell-binding domain of the fibronectin molecule i.e., amino acid 79 to 103, in terms of the Pierschbacher numbering sequence, namely, -Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp and Y is a hydrogen atom or a methionine residue.

DETAILED DESCRIPTION OF THE PREFERRED EMBODIMENTS

Preferred proteins amongst these are those in which n is 1, 2, 3 or 4, X is a part-sequence composed of 10-20 amino acids, and Y is a hydrogen atom.

The new proteins can be prepared by a. preparing a vector which contains the genetic information for the protein as claimed in claim 1,
b. propagating the vector,
c. incorporating the signals necessary for expression into the vector,
d. inserting the vector into a host organism, and
e. propagating the host organism and isolating the protein.

The preparation of a suitable vector starts from the appropriate cDNA.

For the isolation of the appropriate cDNA, the monocyte cell line HL 60 (ATCC No. CCL 240) was cultivated as described [Pennica et al., Nature 312

(1984), 724–729] and, after stimulation, the mRNA was isolated and converted into cDNA by known processes.

A cDNA library was constructed by insertion of this cDNA into the commercially available cloning vector Lambda gt 10.

Figure 1:
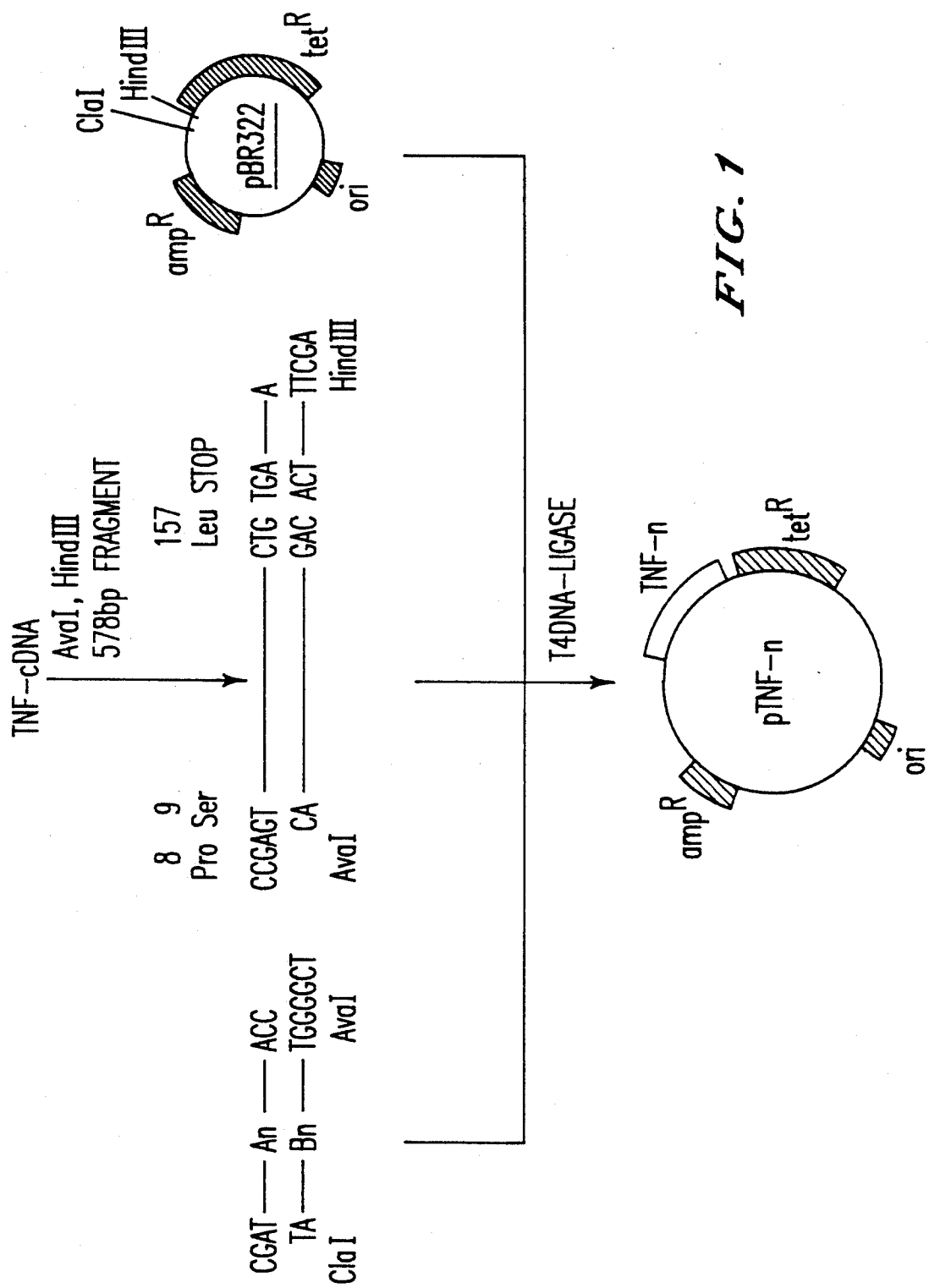
FIG. 1: Construction of plasmids (pTNF-n) which code on expression for fusion proteins of fibronectin and TNF. A ClaI-AvaI linker consisting of the oligonucleotides A$_n$ and B$_n$ is ligated to the ClaI- HindIII fragment of TNF and the resulting ClaI-HindIII-gene is cloned into the vector pBR 322.

Raidiolabeled oligonucleotide probes were used to identify a cDNA clone which contains the coding part of the TNF gene (FIG. 1).

Parts of this sequence, which can easily be obtained by use of restriction recognition sites, are used to clone the novel TNF hybrid genes which are described in detail in the Examples (FIG. 1). The gene fragments were incorporated into cloning vectors, for example into the commercially available plasmids pBR 322 and pBR 327, in a conventional manner. It is also possible for the genes or gene fragments to be provided with suitable chemically synthesized control regions which make expression of the proteins possible. The transformation of the hybrid plasmids obtained in this way into suitable host organisms, advantageously E. coli, is likewise known and described in detail. It is also possible for the hybrid plasmids to be provided with appropriate signal sequences which permit the secretion of the polypeptides into the periplasma of E. coli.

However, because of the degeneracy of the genetic code, it is also possible to utilize other DNA sequences, e.g. chemically synthesized TNF genes with a different DNA sequence, for the expression of TNF hybrid genes.

The novel hybrid proteins with a TNF action can be used as novel active compounds in the therapy of malignant diseases in humans.

EXAMPLES

Preparation of plasmids

1. Preparation of a hybrid plasmid which harbors the gene fragment for a TNF derivative with a modified amino terminus.

The starting material is a recombinant phage which has the cDNA of TNF and was obtained by the process described by Pennica et al. [Nature 312 (1984), 724–729]. For this purpose, the human monocyte cell line HL 60 (ATCC CCL240) was treated with phorbol ester (PMA) to stimulate it to produce TNF. 4 h after the treatment with phorbol ester, the RNA was isolated from this cell line, and the cDNA was prepared from this by the method of Maniatis: Molecular Cloning, Cold Spring Harbor Laboratory, 1982, pages 224 et seq.

This cDNA was used to construct a gene bank, utilizing the lambda phage gt10 as vector. A TNF-specific chemically synthesized radiolabeled oligonucleotide probe was used to screen the gene bank. A clone identified as positive by this was cleaved with the restriction enzymes AvaI and HindIII to give a DNA fragment which is 578 bp in length and encodes amino acids 8 to 157 of the human TNF molecule. This fragment was separated from the other fragments which had been produced by electrophoresis in a 1% strength agarose gel and was eluted from the gel by known processes [Maniatis et al., Cold Spring Harbor Laboratory, page 164, 1982]. The resulting fragment was then incorporated into a vector which had been obtained by cleavage of the plasmid pBR322 with the restriction endonucleases ClaI and HindIII. The large fragment resulting from the cleavage was obtained pure by two ethanol precipitations.

The Cla-Ava adaptor used was an equimolar mixture of synthetically prepared oligonucleotide A1 and B1 having the following primary structure:

A1: 5'-CGATACTACTATGGTCAGATCTTCATCTTCTCGAACC -3'
B1: 3'- TATGATGATACCAGTCTAGAAGTAGAAGAGCTTGGGGCT -5'

The novel hybrid plasmid pTNF-1 was obtained by linking 0.1 pmol of the vector fragment, 0.2 pmol of the TNF fragment 578 bp in length, and 0.5 pmol of each of A1 and B1 using the enzyme T4 DNA ligase (FIG. 1, An and Bn in this denote the oligonucleotides A1, A2 . . . and B1, B2 . . . ).

2. TNF derivatives with a modified amino terminus

The construction was carried out similarly to Example 1 using the novel oligonucleotides A2/B2, A3/B3 and A4/B4:

A2: 5'-CGATACTACTATGGTCAGATCTAGATCATCTTCTTCGCGAACC -3'
B2: 3'- TATGATGATACCAGTCTAGATCTAGTAGAAGAAGCGCTTGGGGCT -5'

A3: 5'-CGATACTACCATGGTCTACGCTGTCACCGGCCGTGGTGACTCTCCTGCTTCA-
B3: 3'- TATGATGCTACCAGATGCGACAGTGGCCGGCACCACTGAGAGGACGAAGT
          TCTTCTCGAACC           3'
          AGAAGAGCTTGGGGCT -5'

A4: 5'-CGATACTACCATGGTCTACGCTGTCACCGGCCGTGGTGACTCTCCTATCGACGGTCGA
B4: 3'- TATGATGGTACCAGATGCGACAGTGGCCGGCACCACTGAGAGGATAGCTGCCAGCT
          ACC-3'
          TGGGGCT-5'

The novel hybrid plasmids pTNF-2, pTNF-3 and pTNF-4, respectively, were obtained.

Figure 2:
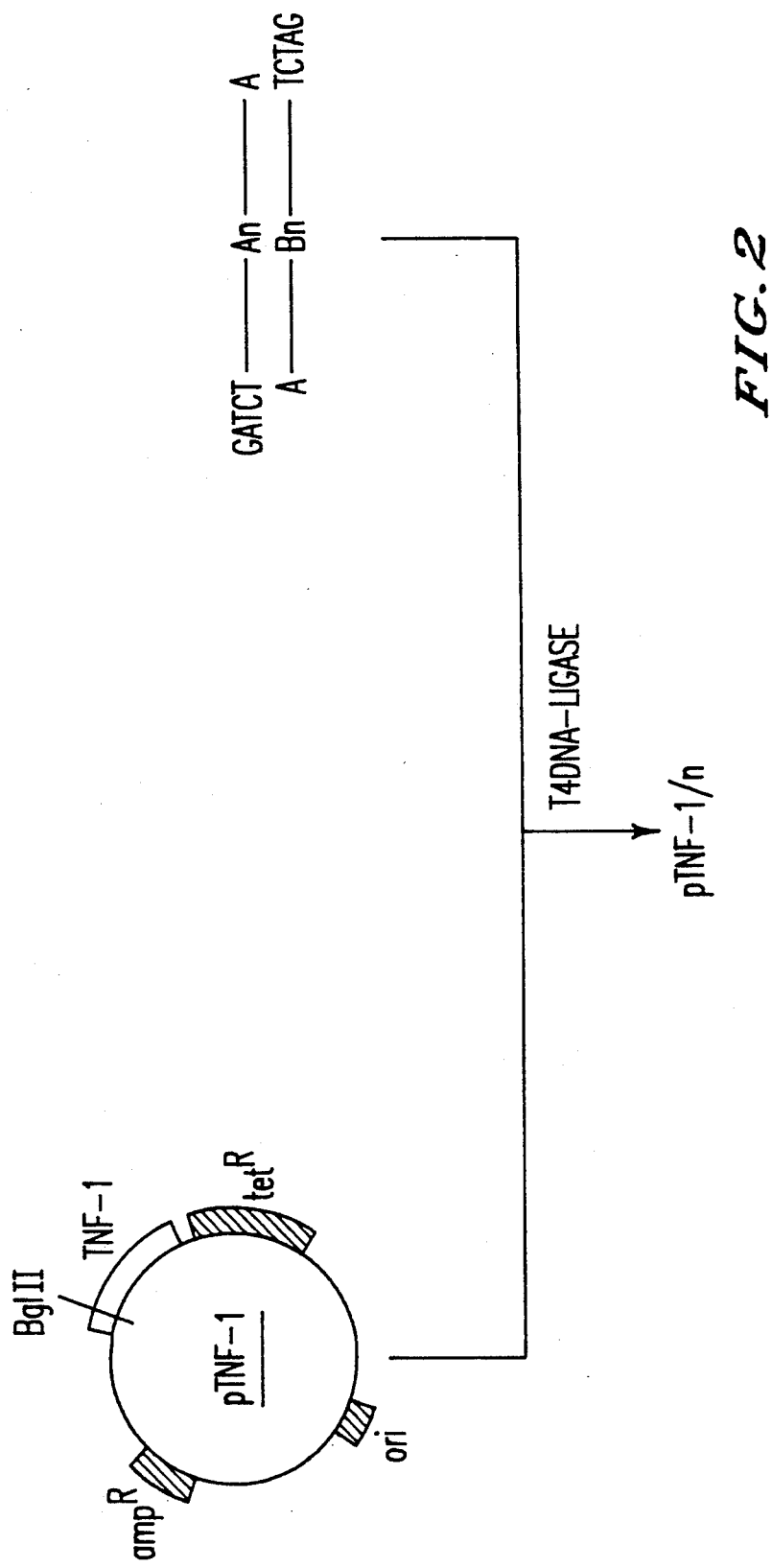
FIG. 2: The plasmid pTNF-1 is cleaved at its unique BglII site and a synthetic DNA fragment, consisting of A$_n$ and B$_n$, is cloned into the BglII site. According to the sequence of A$_n$ and B$_n$ various genes coding for fibronectin-TNF fusion proteins are created.

3. Preparation of hybrid plasmids which harbor the gene fragments for fibronectin-TNF hybrid proteins The starting point is the plasmid pTNF-1 constructed in Example 1. This has a unique BglII recognition site (AGATCT). The plasmid pTNF-1 was opened with the restriction enzyme BglII. 0.3 pmol of an equimolar mixture of synthetically prepared A5 and B5 was added to 0.1 pmol of this DNA fragment and linked by a reaction catalyzed by T4 DNA ligase (FIG. 2).

A5: 5'-GATCTGTCACCGGCCGTGGTGACTCTCCTGCTA -3'
B5: 3'- ACAGTGGCCGGCACCACTGAGAGGACGATCTAG -5'

The novel hybrid plasmid pTNF-1/5 was obtained. It is possible in this construction to incorporate the A5/B5 fragment into the vector in any desired orientation. For this reason, two different hybrid plasmids were obtained, and these differ in the orientation of A5/B5 fragment and, on subsequent gene expression, produce different hybrid proteins. The orientation can be determined by known DNA sequencing methods.

4. Preparation of hybrid plasmids which harbor gene fragments for other fibronectin-TNF hybrid proteins The construction is carried out similarly to Example 3 using the novel oligonucleotide mixtures A6/B6 A and A7/B7:

A6: 5'-GATCTTACGCTGTCACCGGCCGTGGTGACTCTCCTGCTAGCTCAAAGCCTA -3'
B6: 3'-     AATGCGACAGTGGCCGGCACCACTGAGAGGACGATCGAGTTTCGGATCTAG -5'

A7: 5'-GATCTTACGCTGTCACCGGCCGTGGTGACTCTCCTGCTAGCTCAAAGCCT
B7: 3'-AATGCGACAGTGGCCGGCACCACTGAGAGGACGATCGAGTTTCGGA

ATCAGCATCAACTACCGTACCGAAATCGACGGTA  -3'
TAGTCGTAGTTGATGGCATGGCTTTAGCTGCCATCTAG -5'

The novel hybrid plasmids pTNF-1/6 and pTNF-1/7, respectively, were obtained.

Propagation of the plasmids

5. Transformation of the hybrid plasmids

Transformation-competent *E. coli* cells were transformed with 0.1 to 1 μg of the hybrid plasmids from Examples 1 and 4 and were plated out on ampicillin-containing LB agar plates. It was then possible for clones containing correctly integrated TNF part-sequences to be identified by rapid plasmid analysis [Maniatis et al., Cold Spring Harbor Laboratory, 1982, page 366].

6. Production of the proteins

The hybrid plasmids prepared in the above examples are opened at the ClaI site and provided with synthetically prepared signal sequences for gene expression.

The resulting hybrid plasmids were used to transform competent *E. coli* cells [maniatis et al., Cold Spring Harbor Laboratory, 1982, pages 249 et seq.]. The transformed host organism was cultured in LB nutrient medium at 37° C. overnight.

7. Purification of the proteins 1 l of fermentation broth of a *E. coli* strain producing a novel substance was centrifuged at 3000×g for 30 min. The residue was taken up in 200 ml of 0.4M arginine hydrochloride, 20 mM sodium phosphate, pH 8.5, and sonicated for 30 min. 6 ml of 2M $MnCl_2$ were added to the suspension, and the mixture was centrifuged at 3000×g for 45 min. Dilute $NH_3$ solution was used to adjust the supernatant to pH 8.9, and it was 60% saturated using solid ammonium sulfate.

The protein precipitate was suspended in 0.2M arginine hydrochloride, pH 7.5, and dialyzed against 0.4M arginine hydrochloride, pH 7.5. After 16 h, the pH was adjusted to 8.5 with dilute $NH_3$ solution, and the volume was increased 5-fold by dilution with water.

This solution was chromatographed on a ®Sepharose column (Pharmacia) equilibrated with 0.01M arginine buffer, pH 8.5. Elution was with 0.02M Na phosphate and 0.06M NaCl. The eluate was diluted 2.5-fold and then chromatographed on a ®Sepharose column (Pharmacia) equilibrated with 0.02M Na phosphate, pH 8.0. The column was washed with equilibration buffer and then eluted with 0.05M Na phosphate, 0.1M NaCl, 0.1M arginine, pH 8.6, to obtain protein which was pure by SDS polyacrylamide gel electrophoresis.

In this way, the following compounds of the formula as claimed in claim 1 were obtained: (n=4, Y=Met):

A. X = ArgSerSerArgArgValThrThrAlaGlyAspArg
B. X = ArgSerTyrAlaValThrGlyArgGlyAspSerProAlaSerSerLysProArg
C. X = ArgSerTyrAlaValThrGlyArgGlyAspSerProAlaSerSerLysPro-IleSerIleAsnTyrArgThrGluIleAspGlyArg.

8. Cytotoxic activity of the novel polypeptides $5 \times 10^3$ cells which were in exponential growth and had been freshly trypsinized were plated out in 150 μl of complete growth medium (MEM with Earle's salts + 10% strength FCS, Flow Laboratories, Meckenheim) in 96-well plates and incubated at 37° C., 5% $CO_2$ in a water vapor-saturated atmosphere overnight. The substance was added the next day in 25 μl of complete culture medium per culture well. The initial concentration was 10 ng/ml; determination was by duplicate titration with serial 2-fold dilutions. The following controls were included on each culture plate: a) only culture medium; b) cells with culture medium but without substance; c) a titrated TNF standard of known biological activity. After further incubation for 48 h under the conditions indicated above, the surviving cells were stained with a crystal violet solution (15 g of crystal violet, 7 g of NaCl, 646 ml of ethanol and 172.8 ml of 37% strength formaldehyde made up to 2 l with $H_2O$). For this purpose, after the culture medium had been removed by aspiration, the cells were mixed with 50 μl of the staining solution at room temperature for 20 min. The culture plates were then washed with water until all unbound portions of the dye had been removed. The stained cells were lyzed by addition of 100 μl of lysis solution (50% ethanol, 0.1% acetic acid) and measured in a photometer at 540 nm. This resulted in the following activities for the substances in the tested cell lines, expressed in units per mg of protein. One unit is the amount of substance which induces 50% lysis of the treated cells.

| Substance | Biological activity in units per mg of protein from | | |
|---|---|---|---|
| | L-929 | WEHI-164 | MDF-7 |
| rHn-TNF | $8.2 \times 10^6$ | $7.9 \times 10^5$ | $2.6 \times 10^5$ |
| A | $2.0 \times 10^7$ | $1.3 \times 10^6$ | $7.5 \times 10^5$ |
| B | $1.8 \times 10^7$ | $1.6 \times 10^6$ | $9.5 \times 10^5$ |

In the table:
L-929 denotes a mouse fibrosarcoma cell line, WEHI-164 likewise denotes a mouse fibrosarcoma cell line, MCF-7 denotes a human mammary carcinoma cell line, rHn-TNF denotes recombinant human TNF.

We claim:

1. A protein having the following amino acid sequence:

Y—Val—X—(Ser)$_n$—ArgThrProSerAspLys

ProValAlaHisValValAlaAsnPro

GlnAlaGluGlyGlnLeuGlnTrpLeuAsnArg

ArgAlaAsnAlaLeuLeuAlaAsnGly

ValGluLeuArgAspAsnGlnLeuValValPro

SerGluGlyLeuTyrLeuIleTyrSer

GlnValLeuPheLysGlyGlnGlyCysProSer

ThrHisValLeuLeuThrHisThrIle

SerArgIleAlaValSerTyrGlnThrLysVal

AsnLeuLeuSerAlaIleLysSerPro

-continued
CysGlnArgGluThrProGluGlyAla

GluAlaLysProTrpTyrGluProIleTyrLeu

GlyGlyValPheGlnLeuGluLysGlyAspArg

LeuSerAlaGLuIleAsnArgProAsp

TyrLeuAspPheAlaGluSerGlyGlnValTyr

PheGlyIleIleAlaLeu.

in which n is 0, 1, 2, 3 or 4, X is -Tyr-Ala-Val-Thr-Gly-Arg-Gly-Asp -Ser-Pro-Ala-Ser-Ser-Lys-Pro-Ile-Ser-Ile-Asn-Tyr-Arg-Thr-Glu-Ile-Asp- or part thereof having sufficient length to bind to human fibronectin, and Y is a hydrogen atom or a methionine residue.

2. A protein as claimed in claim 1, wherein Y is a hydrogen atom.

* * * * *